United States Patent [19]

Butterfield

[11] Patent Number: 4,710,163

[45] Date of Patent: Dec. 1, 1987

[54] DETECTION OF FLUID FLOW FAULTS IN THE PARENTERAL ADMINISTRATION OF FLUIDS

[75] Inventor: Robert D. Butterfield, San Diego, Calif.

[73] Assignee: Ivac Corporation, San Diego, Calif.

[21] Appl. No.: 872,086

[22] Filed: Jun. 6, 1986

[51] Int. Cl.$^4$ .............................................. A61M 5/00
[52] U.S. Cl. ............................ 604/65; 128/DIG. 13; 604/67
[58] Field of Search ............... 128/DIG. 13; 604/50, 604/65, 66, 67, 245; 137/551, 557

[56] References Cited

U.S. PATENT DOCUMENTS

| 4,525,163 | 6/1985 | Slavik et al. | 604/65 X |
| 4,526,574 | 7/1985 | Pekkarinen | 604/65 X |
| 4,534,756 | 8/1985 | Nelson | 604/65 X |
| 4,553,958 | 11/1985 | Le Cocz | 604/67 |
| 4,617,014 | 10/1986 | Cannon et al. | 604/67 |

Primary Examiner—Edward M. Coven
Attorney, Agent, or Firm—Fulwider Patton Rieber Lee & Utecht

[57] ABSTRACT

This invention is directed to a method and system for evaluating the fluid communication between a parenteral fluid delivery system and a patient's blood vessel. In accordance with the invention, one or more fluid flow pulses are applied to the fluid within the delivery system. Both positive and negative fluid flow pulses may be applied. The pressure response to the pulses under conditions of normal, unimpeded fluid flow is significantly different than the pressure response to such pulses when an infiltration or other fluid flow fault has occurred and this difference is used to detect fluid faults.

20 Claims, 19 Drawing Figures

DETECTION OF FLUID FLOW FAULTS IN THE PARENTERAL ADMINISTRATION OF FLUIDS

BACKGROUND OF THE INVENTION

This invention generally relates to a method and system for monitoring the infusion of parenteral fluids through a fluid delivery system to a patient and, particularly, to the evaluation of the fluid communication between the fluid delivery system and the patient's blood vessel to ensure proper fluid flow.

Fluid delivery systems for infusing parenteral fluids to a patient by means of an infusion pump have enjoyed widespread usage in hospitals. Such systems typically include a bottle of parenteral fluid and an intravenous (IV) set comprising a drip chamber with a piercing element at one end adapted to be inserted through the sealed end of the bottle of parenteral fluid, clear plastic tubing attached to the discharge end of the drip chamber, and means to mount an indwelling cannula on the distal end of the tubing. The cannula mounted at the distal end of the tubing is adapted to be inserted into the patient's blood vessel to thereby deliver parenteral fluid. Roller clamps to manually control fluid flow rates, injection sites, and pressure diaphragms may also be provided with the IV set. The infusion pump is either a piston actuated type pump or a peristaltic type pump wherein a plurality of rollers, cams, or cam-actuated fingers sequentially constrict the flexible plastic tubing of the IV set to drive the parenteral fluid through the tubing.

While these systems have gained widespread acceptance, one common problem with commercially available systems is the difficulty in evaluating the fluid flowing therein in order to detect improper fluid communication between the fluid delivery system and the patient's blood vessels. Generally, if a fluid flow fault develops, the infusion pump will continue to deliver parenteral fluid notwithstanding such fluid flow fault. Thus, for example, if the needle delivering fluid to the patient becomes dislodged from the vein so that the discharge tip of the needle lies in adjacent interstitial tissue, the fluid, which continues to be pumped, infiltrates the interstitial tissue, and may cause serious injury. If the needle becomes completely dislodged from the patient, i.e., an open line, there may be no immediate injury, but the patient does not receive the fluid or drugs needed for treatment. In addition to the above fluid flow faults, other malfunctions of fluid delivery system including air-in-line and occluded tubing or needles.

Detection systems have been developed which sound an alarm or turn off the infusion pump or both when the pressure detected in the parenteral fluid delivery system is greater or less than predetermined maximum and minimum set points. While these control systems have been helpful in some circumstances, they are unable to detect a wide variety of malfunctions in the fluid delivery system. Moreover, these prior systems frequently could not distinguish between fluid flow faults and natural fluid pressure variations within the tubing, and this inability to discriminate resulted in many false alarms.

The method and system described and claimed by Nelson in U.S. Pat. No. 4,534,756 assigned to the present assignee, was a substantial advance in the art of controlling the administration of parenteral fluids to a patient and, particularly, for detecting fluid flow faults in such a system. The method and system described could quickly respond to malfunctions and could distinguish between normal pressure variations and many of the malfunctions normally encountered in the use of such delivery systems.

However, the system of Nelson frequently was not effective in discriminating between fluid flow faults and normal pressure variations at high fluid flow rates. As a result, the need remains for fluid flow fault detection over a wider range of fluid flow conditions particularly at higher fluid flow rates and for better discrimination between normal pressure variations and malfunctions of the delivery system. The present invention satisfies these needs.

SUMMARY OF THE INVENTION

This invention is directed to the monitoring of fluid flow in the administration of parenteral fluids to a patient and, particularly, to a method and system for evaluating the fluid communication between a parenteral fluid delivery system and a patient's blood vessel in order to detect fluid flow faults.

In accordance with the system of the invention, means are provided to apply fluid flow excitation pulses of predetermined magnitude and duration to fluid in a delivery system. As used herein, the term "pulse" and terms of similar import refer to fluid flow of short duration. The fluid pressure in the delivery system is monitored by pressure sensing means in order to detect or sense the natural dynamic pressure response of the fluid delivery system to the applied pulses and to generate a signal representing the sensed pressure response or a characteristic thereof. The system also includes means to generate and preferably store a reference signal representing the pressure response or a characteristic thereof of fluid in the delivery system to a fluid flow pulse of the same predetermined magnitude and duration when there is fault-free fluid communication between the fluid delivery system and the patient. The signal representing the sensed pressure response or characteristic thereof is compared with the reference signal representing the standard or normal response or characteristic thereof and, if the differences or deviations therebetween exceed predetermined limits, improper fluid communication between the fluid delivery system and the patient's vein is indicated and a signal is generated by means responsive to the difference to activate an alarm. If desired, a fluid flow control function can also be effected, such as turning off the pump.

The reference signal is preferably developed by applying an excitation pulse of the predetermined magnitude and duration to fluid in the delivery system at the time of cannular needle placement when normal fault-free fluid can be assured and can be readily checked. The natural response of the fluid delivery system to the applied excitation pulses will be described herein as a pressure response, although it is to be recognized that other parameters related thereto or desirable therefrom may also be used. Moreover, the term "natural response" or "transient response" or words of similar import shall include all or a significant part of the pressure response to the fluid pulse or a characteristic thereof.

The magnitude of the pressure response resulting from the excitation pulse should be significantly different from a baseline fluid flow condition in order to consistently distinguish the pressure response caused by the pulse from the normal pressure variations encountered in the fluid delivery system. Generally, it has been found that the pressure of the pulses should exceed the baseline pressure level by at least 15 percent and preferably by at least 20 percent of the normal or baseline pressure level. However, the excitation pulses should be of short duration and small volumes so as to not effect any significant changes in the fluid flow rate in the fluid delivery system. In a preferred embodiment, the pulse is applied during periods when essentially no fluid flow is occurring. The entire period for detecting fluid flow faults should not exceed 20 percent, preferably 10 percent, of the total fluid pumping time.

The excitation flow pulses applied to the fluid in the fluid delivery system can be either positive or negative, i.e., drawing fluid to the patient or withdrawing it. Moreover, a series of pulses of short duration may be used for a single pulse longer duration.

By applying excitation flow pulses of known magnitude and duration in accordance with the invention, the transient pressure response of the fluid in the fluid delivery system thereto can be readily compared with a a predetermined transient response of fluid in the delivery system to a pulse of essentially the same magnitude and duration under fault-free fluid flow conditions in order to detect improper fluid communication between the fluid delivery system and the patient. However, in each case, sufficient time should be allotted after each test pulse or group thereof to allow the transient pressure response to decay before resuming regular fluid pumping. Typical time periods for the transient response to decay vary, but usually are less than about 100 miliseconds and by alloting from about 0.1 to about 0.5 seconds between the excitation pulse and subsequent pumping activity, the interference therebetween can be minimized.

A wide variety of ways can be employed to compare a signal representing the sensed pressure response to an applied pulse with a reference signal representing the standard pressure response under fault-free fluid flow conditions. Preferably, the signal representing the sensed transient response and the reference signal are compared by means of a subtractive measure of error method (SMOE) which provides an indication of the alikeness of complex signals. This procedure is in essence a numerical integration of the area between pressure-time curves representing the two pressure responses. A SMOE value of zero would indicate that the two responses were identical, whereas larger absolute sums indicate greater differences, and greater differences indicate fluid flow faults between the fluid delivery system and the patient. Usually, one of the response signals is scaled in order to properly compare the differences between the two signals.

In a preferred embodiment, means are provided to detect short-term variations in pressure, commonly termed "noise," which is used to modify the SMOE value to thereby eliminate many false alarms.

Other methods of comparing the sensed and standard response signals can be used including cross correlations or fourier analysis of the transient response.

The method and system of the present invention provides for the rapid and discriminating detection of fluid flow faults in parenteral fluid delivery systems, such as infiltration, air-in-line fluid, and occlusions. These and other advantages of the invention will become more apparent when taken in conjunction with the following detailed description and the accompanying exemplary drawings.

BRIEF DESCRIPTION OF THE DRAWINGS

In the drawings, corresponding parts are numbered the same.

DETAILED DESCRIPTION OF THE INVENTION

Figures 1, 2:
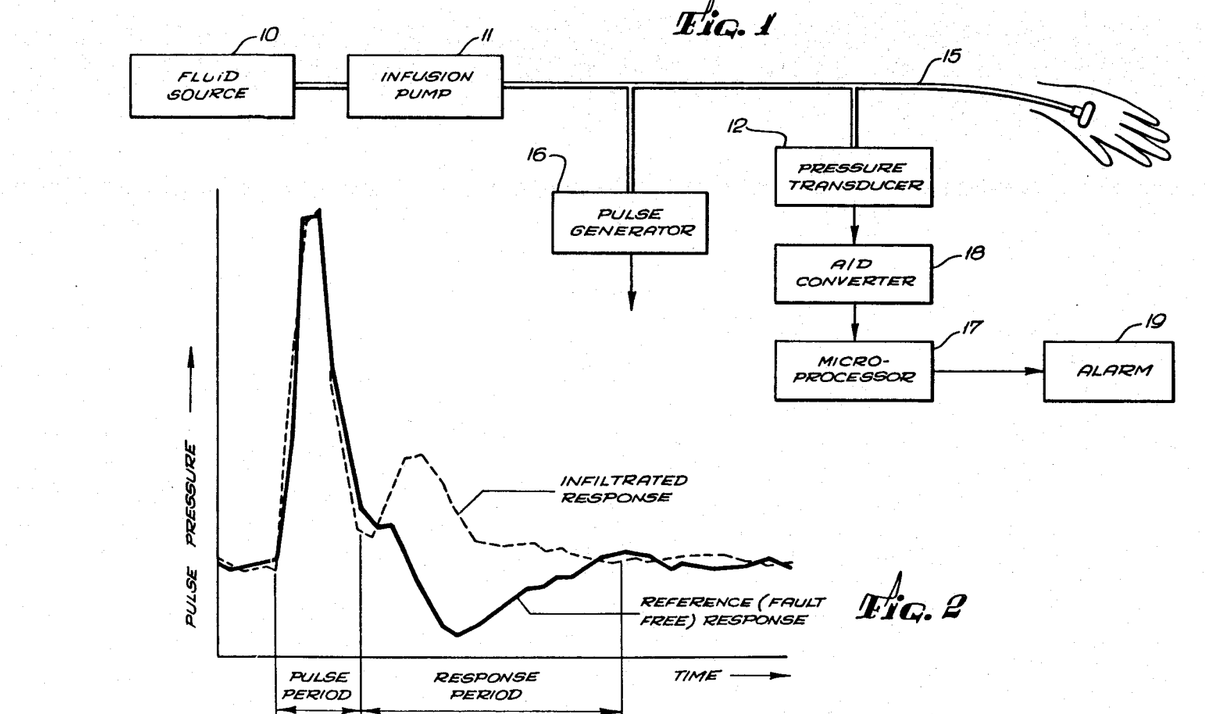
FIG. 1 is a simplified block drawing of a fluid delivery system embodying features of the invention.
FIG. 2 is a graphical representation of the pressure wave forms for a sensed pressure response during an infiltration to a fluid flow excitation pulse and a reference pressure response during normal fluid flow to a fluid flow excitation pulse of essentially the same magnitude and duration to illustrate the differences therebetween.

Reference is made to FIG. 1 which illustrates in a schematic fashion a parenteral fluid delivery system which embodies features of the invention. The fluid delivery system generally comprises a source 10 of parenteral fluid, a peristaltic pump 11, a pressure sensor or transducer 12, and a needle or cannula 13 for delivery of fluid to a blood vessel in a patient's hand 14. Tubing 15 is connected to the discharge end of a drip chamber (not shown) which is connected to the fluid source 10 which is typically an inverted bottle or container (not shown) holding parenteral fluid. A fluid pulse generating unit 16 is provided to apply fluid pulses of known magnitude (volume) and duration to the fluid within the delivery system. The fluid pulse generating unit 16 is shown in FIG. 1 as a separate unit because it has a function separate from the primary function of the pump 11, but with most systems the pumping element 11 may be controlled to perform the function of applying excitation pulses to fluid in the delivery system.

A microprocessor 17 is programmed to activate the fluid pulse generating unit 16 to apply the excitation pulses to fluid in the fluid delivery system of a predetermined magnitude and duration and at the time desired.

The pressure sensor or transducer 12 monitors the pressure of the fluid within the tubing 15 and generates analog signals representing the pressure sensed. These analog signals are passed to an analog-to-digital signal converter 18 where they are digitized and the digitized signals are transmitted to microprocessor 17. The microprocessor 17 compares the pressure signal representing the sensed transient pressure responses to applied excitation fluid flow pulses with a stored reference signal representing a standard transient pressure response to excitation pulses of essentially the same magnitude, and duration under conditions of known fault-free fluid flow through the fluid delivery system. If the comparison shows significant differences, fluid flow malfunction is indicated and a signal is generated by the microprocessor 17 to activate alarm 19 and a control unit (not shown) if desired.

To facilitate the comparison, the microprocessor 17 is preferably programmed to store, as a standard or reference signal, a signal representing an actual transient pressure response of the fluid delivery system to a pulse of the predetermined magnitude and duration when the operator knows that fault-free fluid flow exists. This is accomplished by the operator entering instructions to the microprocessor 17 to store the signal representing the transient response when a pulse is applied under fault-free fluid flow conditions. Other reference signals may be used such as signals representing idealized reference transient responses or responses which have been calculated from a mathematical model of the fluid delivery system.

A presently preferred method and system for detecting the difference between the sensed transient response of the fluid delivery system with a reference response under normal fluid flow conditions is by a procedure of subtractively measuring the error or difference (SMOE) between the sensed signal and the reference signal. The SMOE factor (i.e., the alikeness) is a function of the sum of the absolute value of the differences between the signal representing the sensed response and the reference or standard signal. This method is in essence a numerical integration of the area between the time-pressure curves of the sensed transient response and the standard or reference transient response and follows the general equation:

$$SMOE = \sum_{T_1}^{T_n} |S(t) - R(t)|$$

where
SMOE is the error function;
S(t) represents the sensed transient response signal or characteristic thereof; and
R(t) represents the standard or reference transient response signal or characteristic thereof.

An expression $-S(t_1)+R(t_1)$ is preferably included in the absolute sum to compensate for baseline offset variations which may occur between successive responses. FIG. 2 graphically represents such a calculation with the area between the two curves being the SMOE factor. The sensed response period shown in FIG. 2 after the pulse period which represents the natural pressure-time curve characteristic of an infiltration. The SMOE function has a minimum value of zero when the two transient responses match in shape, i.e., the curves essentially overlap. The higher the SMOE factor, the greater is the area between the curves, and the greater is the indication of a fluid flow fault such as an infiltration.

Figure 3:
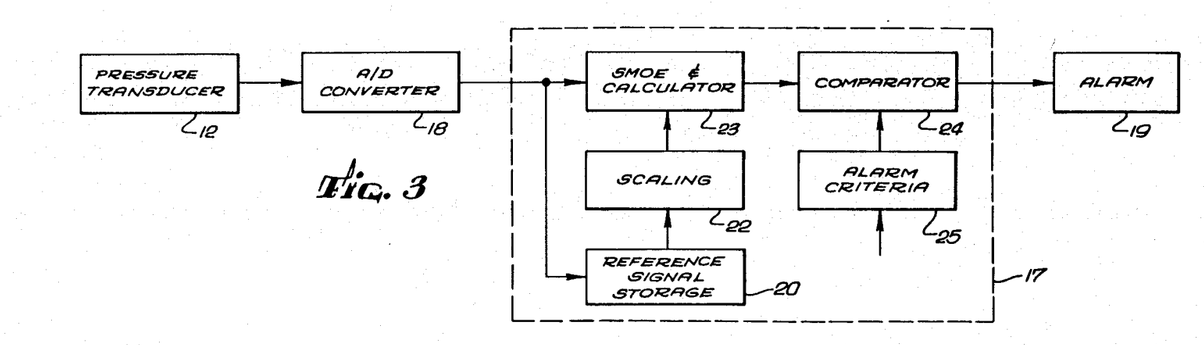
FIG. 3 is a schematic diagram illustrating a system to compare a sensed pressure response to a fluid flow pulse with a reference pressure response to a fluid flow pulse of essentially the same magnitude and duration.

FIG. 3 represents a schematic diagram of a suitable comparison system in more detail. In this system, transient pressure response caused by applied excitation pulses are sensed by the transducer or sensor, appropriate signals are generated and then digitalized in A/D converter 18. If a particular transient pressure response detected is to be used as the standard or reference pressure response, the pressure signals representing it are directed to reference signal storage unit 20 for subsequent comparative use.

In order to ensure that the excitation flow pulses used for creating the reference transient pulse pressure response and those used for subsequent signal of the same magnitude, duration, and have the same flow pattern, the microprocessor should be programmed to actuate the pump 11 to create the pulses at the same mechanical positions thereof so that the variations in fluid flow pulses due to mechanical tolerances of the pump can be minimized. Alternatively, a scaling unit 22 may be employed to appropriately scale the standard signal pattern to facilitate accurate comparisons.

With reference to FIG. 2, the pressure signals shown comprise two different sections, the first representing the pulse driven pressure response and the second the natural pressure response of the delivery system to the pulse. In order to properly compare the two natural pressure response curves, the two pulse driven response curves should track or match as to starting pressure and the time thereof and the peak pressures and the time thereof. By scaling one of the curves so that the pulse portion of the two curves match and accurate comparison can be made of the natural pressure response either the reference signal or the sensed signal may be scaled.

The signals representing the sensed pressure wave pattern and the signals representing the reference or standard pressure wave pattern are fed to the SMOE calculator 23 which calculates the SMOE factor as previously described and the calculated SMOE value are then transmitted to comparator 24 where the calculated SMOE value is compared with a predetermined maxiumm value from alarm criteria 25. If a signal is generated to activate the alarm unit 19 so that medical personnel can correct the fluid flow fault. If desired, the signal generated can be used to actuate a control function such as turning off or otherwise controlling the pumping unit 11 in addition to or in lieu of activating an alarm. The alarm may be audial or visual.

To minimize the effects of noise on the sensed response and the subsequent SMOE calculations, it has been found that a measure of noise can be employed to modify the SMOE value so that effective fault detection can still be maintained with high noise levels. In this method an indication of fluid flow faults identified as Measure of Infiltration (MOI) is defined by the equation:

$$MOI = \frac{SMOE}{1 + Noise}$$

Figure 4:
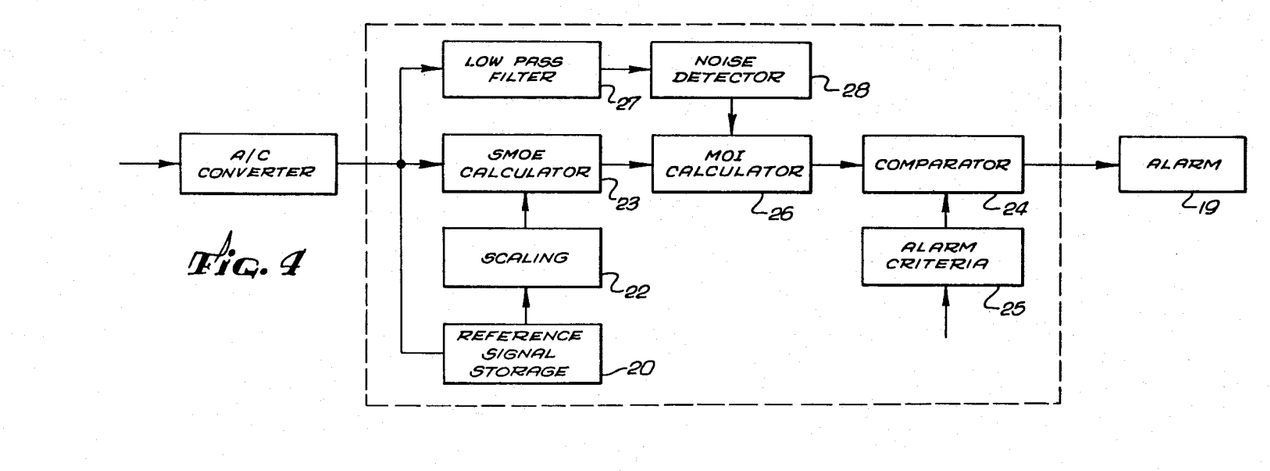
FIG. 4 is a simplified block diagram illustrating in more detail the means to calculate the measure of infiltration.

A system for determining and use of the MOI value is schematically illustrated in FIG. 4 which is similar in many respects to FIG. 3. The SMOE value is calculated in SMOE calculator 23, as previously described, and a signal representing the calculated SMOE value is directed to MOI calculator 26. Signals representing the pressure variations during the period preceding the pulse period are passed through filter 27, preferably a bandpass filter passing about 0.25 to about 10 Hz, and noise detector 28 calculates a noise value from the filtered short-term pressure signal variations and transmits a signal representing the noise value determined to the MOI calculator 26 wherein the MOI is calculated. In comparitor 24 the calculated MOI is compared with a MOI set point (a maximum value) from alarm criteria unit 25 and if the calculated MOI value exceeds the predetermined maximum MOI value, then an infiltration is indicated and a signal is generated to actuate alarm 19 or, if desired, actuate a control function such as turning off the pump 11. The filter 27 is used to eliminate extremely large pressure variations, such as occur with patient movement or ambulation and any high frequency electrical noise caused by the pump, the sensor, or other electrical or electronic devices.

Figure 5A:
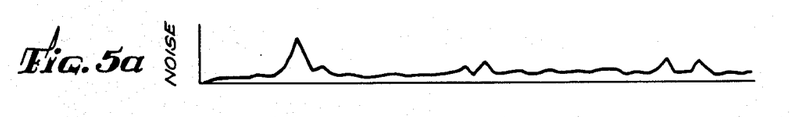
FIGS. 5a, b, c, d represent respectively the noise curve, a SMOE curve, a MOI curve, and a pressure response curve for a particular time period.
Figure 5B:
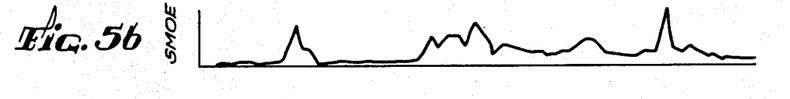
Figure 5C:
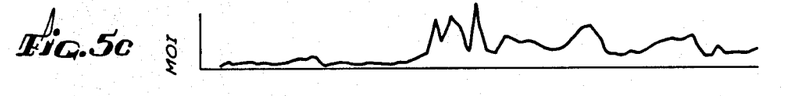
Figure 5D:
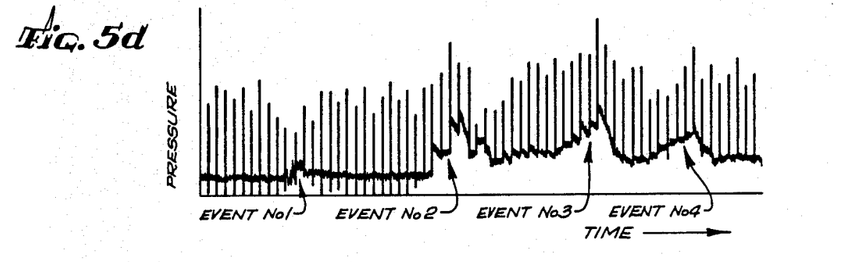
Figure 6A:
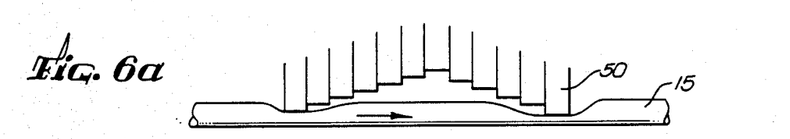
FIGS. 6a, b, c, and d is a schematic drawing illustrating the action of a peristaltic pump on the tubing of a fluid delivery system.
Figure 6B:
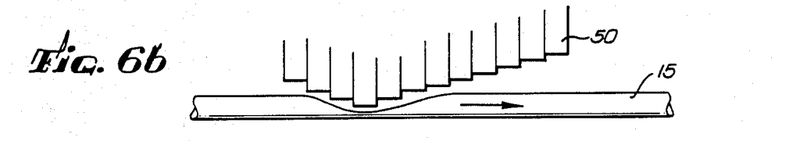
Figure 6C:
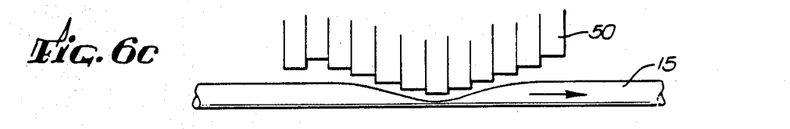
Figure 6D:
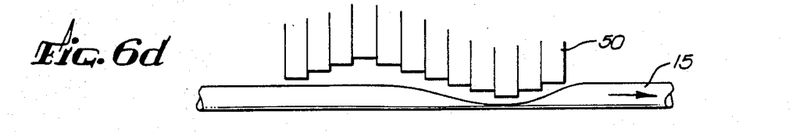

FIGS. 5a, b, and c represent respectively a noise curve, SMOE curve, a MOI curve, and a pressure response curve over the same time period. The purpose of the figures is to illustrate the effectiveness of MOI calculations in eliminating false alarms of infiltrations due to excessive noise. FIG. 5d shows the pressure response of the periodic excitation fluid pulses. Event No. 1 involves a high SMOE value due to excessive noise. Note that there is little or no change in MOI value. In Event Nos. 2 and 3, the high SMOE value truly represented an infiltration which is shown by the high MOI value. In Event No. 4 the high MOI value still distinguished an infiltration not-withstanding the high noise level.

FIGS. 6a–d schematically represent the action of a peristaltic pump 11 wherein a plurality of rollers, cams or cam-actuated fingers 40 sequentially constrict the plastic tubing 15 to thereby drive a single pulse of fluid through the tubing 15. Generally, the volume of fluid in each pulse is more or less constant and the fluid flow rate of the pump 11 is controlled by adjusting the pulse frequency. The quantity of fluid delivered with each fluid flow pulse typically ranges from about 2 to about 70 microliters depending upon the pump construction. The typical time required for the mechanical action of the pump t(i.e., activation of all of the fingers 40) to deliver one fluid flow pulse is approximately 2 milliseconds. However, the transient pressure response of fluid in most commercially available fluid delivery systems to a fluid pulse may last from about 50 to 150 milliseconds. Thus, at low volume flow rates (low pulse frequency) each transient response usually has time to decay before another pulse is applied, whereas at higher flow rates, each succeeding pulse interferes with the transient response from the preceding pulse which makes analysis thereof to detect fluid flow faults very difficult.

By applying fluid flow pulses of predetermined magnitude to the fluid in the fluid delivery system in accordance with this invention, wherein the magnitude of the flow rate thereof is significantly greater than the baseline flow rate of fluid in the delivery system, the resultant transient pressure response in the case of a malfunction of the fluid delivery system can be more readily distinguished from normal variations in the transient responses of normal fault-free fluid flow. Preferably, the baseline flow rate is at or near zero. It is most important that the reference signal accurately represent the pressure response of the fluid delivery system used under fault-free conditions because minor changes in the delivery system, such as needle size or tubing length or diameter can have significant effects on the transient pressure responses to applied fluid flow pulses.

The volume of each individual fluid pulse or bolus produced by the peristaltic pump is very small, e.g., typically, depending upon the pump type and mode, the volume may range from 0.5 to 10 microliters, and this volume may be inadequate to generate any measurable pressure response in the fluid in the delivery system due to the high level of compliance (elasticity) thereof. Therefore, it is frequently necessary to apply a series or group of pulses as the excitation pulse to the fluid in order to obtain a detectable transient pressure response. As previously described, each of the groups of pulses applied to the delivery system should be of the same magnitude, duration, and frequency of the pulse used to generate the reference transient response. Thus, with all excitation pulses, the same pump elements (rollers, cams, fingers, etc.) should be used to constrict the tube 5 in the same sequence and timing.

Figure 7A:
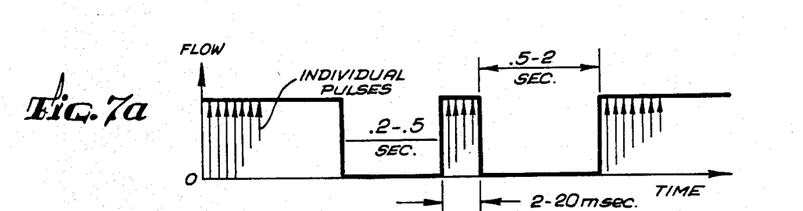
FIGS. 7a and 8a illustrate fluid flow pulse patterns from a peristaltic pump where fluid flow is terminated for short periods and during the flow termination periods one or more fluid flow pulses are applied to the fluid in the system.

FIG. 7 illustrates a preferred excitation pulse pattern wherein the normal fluid flow through the tube 15 to the patient is periodically terminated (i.e., the pump is stopped). A first short period of about 0.2 to 0.5 seconds of essentially zero fluid flow is provided to allow the fluid pressure to decay, then a series of short bursts of fluid flow pulses are applied to the fluid in the fluid delivery system and a second short period of about 0.2 to 0.5 seconds of essentially zero fluid flow is provided to allow the pressure response to the excitation pulse to decay and then normal fluid flow is resumed.

Figure 7B:
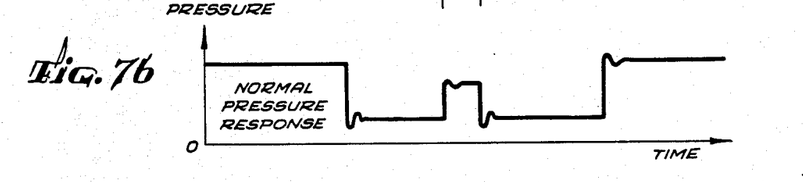
FIGS. 7b and 8b illustrate the resultant pressure response to the pulses shown in FIGS. 7a and 8a under normal flow conditions.
Figure 7C:
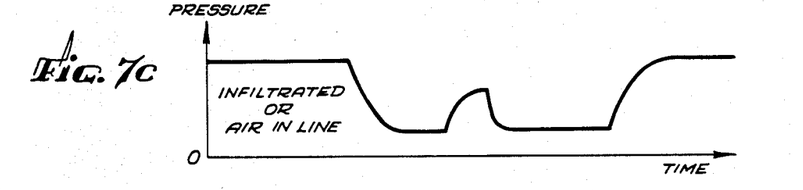
FIGS. 7c and 8c illustrate the resultant pressure response to the pulses shown in FIGS. 7a and 8a under conditions of an infiltration.

FIG. 7b represents the pressure response of the fluid flow pattern shown in FIG. 7a where there is fault-free fluid flow. FIG. 7c, on the other hand, is the pressure response to the fluid flow pattern shown in FIG. 7a where there is an infiltration. The noise values are taken just before the pulse period.

Figures 8A, 8B:
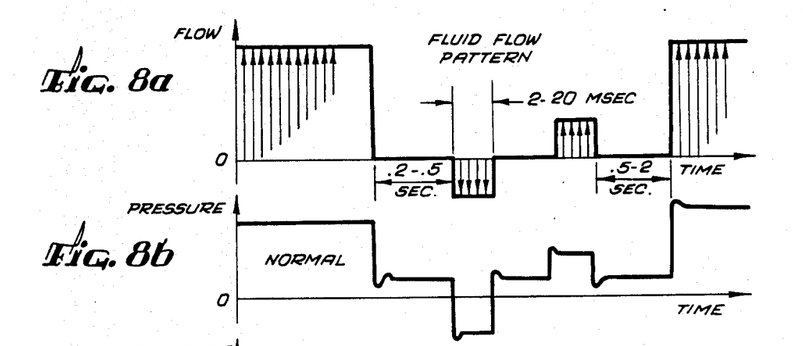
Figure 8C:
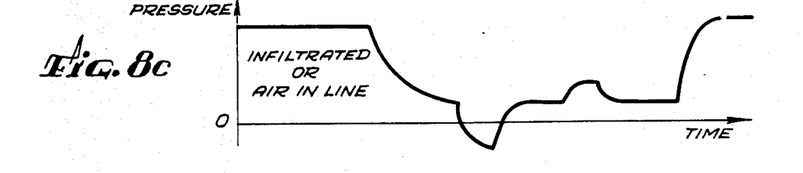

The excitation pulse pattern shown in FIG. 8a is similar to the pattern shown in FIG. 7a, except periods of both negative and positive pulses are applied with similar delay periods provided therebetween. FIG. 8b illustrates the transient pressure responses under normal fault-free fluid flow. FIG. 8c illustrates the transient pressure response resulting from an infiltration. The excitation pulse (usually 2 to 4 pulses) ranges from about 2 to 20 milliseconds and the pause between normal flow and the start of excitation pulse is about 0.2 to 0.5 seconds and between the end of the excitation pulse and the start of normal fluid flow is about 0.5 to 2 seconds. The total time for fluid flow fault detection should not exceed 20 percent, preferably not more than 10 percent, of the total pumping time.

Other flow test patterns can be used, for example, by judiciously adding negative pulses to a continuous sequence of positive pulses of the same magnitude from the pulsatile pump, a resultant short term fluid flow pattern is generated which can approximate a sinusoidal shape similar to an A.C. signal. Some peristaltic pumps can be controlled to provide such a fluid flow pattern. The benefit from this pattern of fluid flow pulses is that calculation of the root means square of the transient pressure response or the peak-to-peak value of the pressure response sensed by the pressure transducer can be sufficient to quantify the state of the fluid delivery system in order to compare with reference values thereof in order to detect a malfunction of the fluid flow to the patient. Another method of analyzing the transient response to an applied sinusoidal fluid flow pattern includes measurement of the frequency response to applied activating pulses at several different frequencies. This procedure is feasible because the frequency response of the fluid delivery system varies with changes in the fluid resistance in the tubing or at the injection site.

Figure 9:
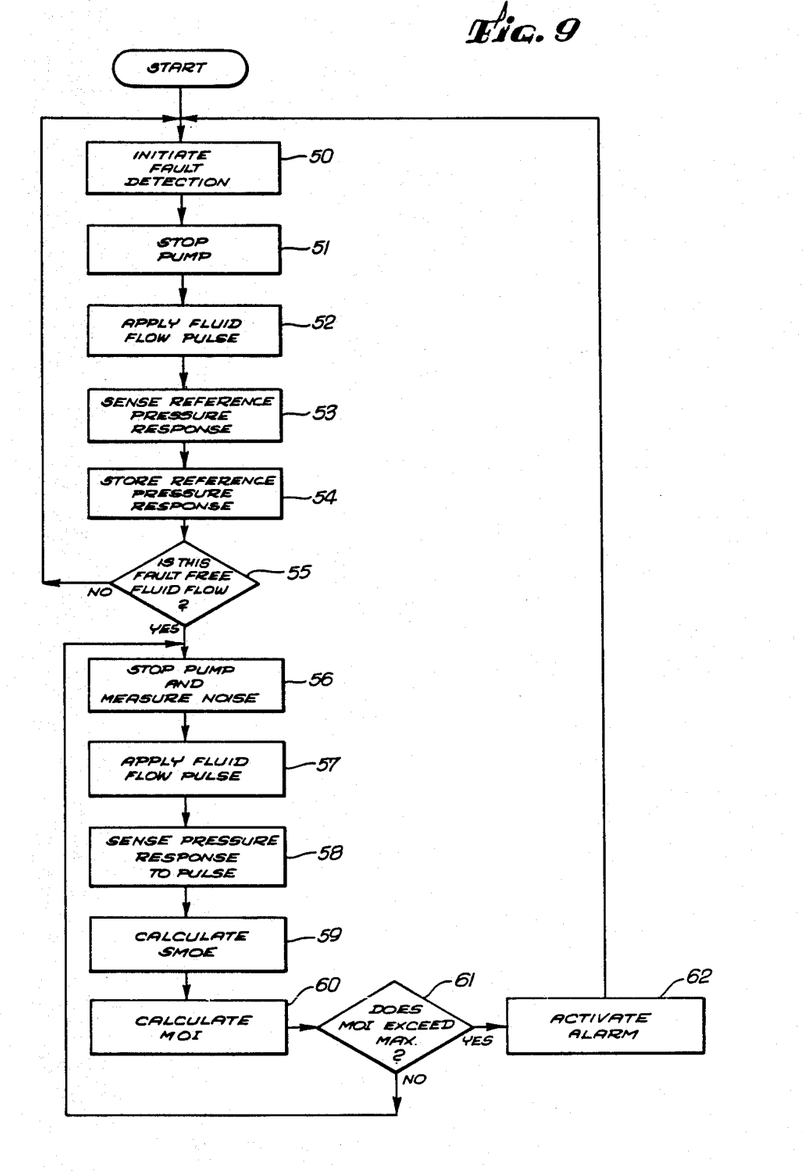
FIG. 9 illustrates a flow chart of the general control algorithm performed by the system.

The operation of a fluid fault system in accordance with the invention is illustrated in FIG. 9 which represents a flow chart of a general algorithm performed by this portion of the control system. At the start, the peristaltic pump is operating in a normal fashion. At step 50 the fault detection system is actuated by the operator activating an appropriate switch on a control panel. Upon actuation of the system, the peristaltic pump is stopped at step 51 and at step 52 the pump is actuated to apply an excitation pulse to the fluid in the fluid delivery system. The pressure response from the applied pulse is sensed at step 53 and stored at step 54. The operator is then required at step 55 to input whether or not the fluid flow is normal and fault-free. If the input is negative, the program requires the operator to reinitiate the fault detection at step 50. If the operator's response is positive, then at step 56 the pump is against stopped and the short-term pressure variation (noise) is detected. After a short delay, the pump is reactivated to apply an excitation pulse to the fluid in the fluid delivery system and at step 58 the pressure response to the pulse is sensed. At step 59 the SMOE value is calculated from the stored reference pressure response from step 54 and the sensed pressure response from step 58. The MOI value is calculated at step 60 from the noise value determined at step 56 and the SMOE value calculated in step 59. If the MOI is greater than the predetermined maximum, the program actuates the alarm at step 62. The operator must then turn off the alarm and reinitiate the infiltration detection system. If the MOI is less than the predetermined maximum value, then the program returns to step 56 where the pump is again stopped and zero flow noise is again determined.

In the aforesaid control procedures, it is assumed that the operator will correctly determine at step 55 whether the fluid flow is fault-free. To minimize such errors, it is preferred to compare the standard or reference pressure response with one or more subsequent pressure responses to determine whether there are significant variations between the responses. If the variations are significant, then it is assumed that the standard pressure response first detected does not represented fault-free fluid flow and the program requires the operator to reinitiate the fault detection system.

It is obvious that various modifications and improvements can be made to the present invention without departing from the scope thereof.

What is claimed is:

1. A system for monitoring the flow of parenteral fluid through a parenteral fluid delivery system to a patient wherein the fluid in the delivery system is at a base level of pressure or flow rate, the system comprising:
   (a) means to apply to fluid in the fluid delivery system a fluid flow excitation pulse which is at a pressure or flow rate significantly greater or lesser than the base level of pressure or flow rate of fluid therein;
   (b) means to sense the pressure response of fluid in the delivery system to the applied excitation pulse and generate a signal representing the response or characteristic thereof;
   (c) means to generate a reference signal representing a pressure response or characteristic thereof of fluid in the delivery system to a fluid flow excitation pulse of a magnitude and duration equivalent to the fluid flow excitation pulse applied in (a) above when fault-free fluid flow conditions into the patient exist;
   (d) means to compare the signal representing the sensed pressure response or characteristic thereof with the signal representing the reference pressure response or characteristic thereof to detect a difference therebetween; and
   (e) means responsive to the difference to generate an alarm signal.

2. The system of claim 1 wherein means responsive to the difference is actuated when the difference between the sensed pressure response signal and the reference pressure response signal exceeds a predetermined amount, the predetermined difference therebetween selected to indicate improper fluid communication between the fluid delivery system and the patient.

3. The system of claim 1 wherein means are provided to determine the differences between a first pressure-time curve representing the sensed pressure response and a second pressure-time curve representing the reference pressure response, the differences representing a numerical integration of the area between the two pressure-time curves.

4. The system of claim 3 wherein the differences are summed absolute values.

5. The system of claim 4 wherein the differences are determined from the equation $$\sum_{T_1}^{T_n} |S(t) - R(t)|$$

wherein
   S(t) is the value of the sensed pressure response at time t;
   R(t) is the value of the reference pressure response at time t.

6. The method of claim 3 wherein the pressure or flow rate of the excitation pulse is at least 15 percent greater than or less than the base level pressure or flow rate of the fluid in the fluid delivery system.

7. The method of claim 3 wherein the pressure or flow rate of the excitation pulse is at least greater than 20 percent greater than or less than the base level pressure or flow rate of the fluid in the fluid delivery system.

8. The system of claim 1 wherein means to apply a fluid flow pulse include means to generate a negative fluid flow pulse to fluid in the fluid delivery system.

9. The system of claim 5 including means to determine the short-term fluid pressure variations, identified as noise, of fluid in the fluid delivery system prior to the application of the fluid flow pulse.

10. The system of claim 9 including means to calculate a factor representing a measure of infiltration (MOI) from the equation:

$$MOI = \frac{SMOE}{\text{Noise} + K}$$

wherein:
   SMOE is the subtractive measure of error as calculated in claim 5;
   Noise is the short-term fluid pressure variations as determined in claim 9, and
   K is a constant or zero.

11. The system of claim 10 wherein the constant K is 1.

12. The system of claim 1 wherein the fluid delivery system includes a pulsatile pump to pump perenteral fluid through the delivery system to the patient.

13. The system of claim 1 wherein means to apply a fluid flow pulse to the fluid delivery system includes means to generate positive and negative fluid flow pulses to fluid in the fluid delivery system.

14. The system of claim 1 wherein the pressure or flow rate of the excitation pulse is at least 15 percent greater than or less than the base level pressure or flow rate of the fluid in the fluid delivery system.

15. The system of claim 1 wherein the pressure or flow rate of the excitation pulse is at least greater than 20 percent greater than or less than the base level pressure or flow rate of the fluid in the fluid delivery system.

16. A method of monitoring the flow of parenteral fluid through a fluid delivery system to a patient, wherein the fluid in the delivery system is at a base level of pressure or flow rate, the method comprising:
   (a) applying to fluid in the fluid delivery system a fluid flow excitation pulse at a pressure or flow rate significantly greater or lesser than the base level of pressure or flow rate of fluid therein;
   (b) sensing the pressure response of fluid in the fluid delivery system to the applied excitation pulse and generating a signal representing the pressure response sensed or characteristic thereof;
   (c) generating a reference signal representing a pressure response or characteristic thereof of fluid in the fluid delivery system having to a fluid flow excitation pulse of a magnitude and duration equivalent to the fluid flow excitation pulse applied in (a) above when fault-free fluid flow conditions into the patient exist;
   (d) comparing the signal representing the sensed response or characteristic thereof with the signal representing the reference pressure response or characteristic thereof to detect a difference therebetween; and
   (e) generating an alarm signal when the sensed response signal differs from the reference response signal in a predetermined manner, the predetermined difference therebetween indicating the nature of the fluid communication between the fluid delivery system and the patient.

17. The method of claim 16 wherein the transient pressure response to an applied pulse of the same magnitude as the excitation pulse under normal fluid flow conditions is calculated from a mathematical model of the fluid delivery system and the injection site.

18. The method of claim 16 wherein the excitation pulse is applied to the fluid in the fluid delivery system by adjusting the fluid flow rate therein to a higher or a lower level.

19. The method of claim 16 wherein the excitation pulse applied to the fluid in the fluid delivery system is in a direction opposite to the direction of the normal fluid flow through the delivery system to the patient.

20. The method of claim 16 wherein the excitation pulse is a series of positive and negative fluid flow pulses which form a fluid flow pattern which is sinusoidal.

* * * * *